US008844792B2

(12) United States Patent
Viola

(10) Patent No.: US 8,844,792 B2
(45) Date of Patent: Sep. 30, 2014

(54) SURGICAL INSTRUMENT WITH CURVILINEAR TISSUE-CONTACTING SURFACES

(71) Applicant: Covidien LP, Mansfield, MA (US)

(72) Inventor: Frank Viola, Sandy Hook, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/668,368

(22) Filed: Nov. 5, 2012

(65) Prior Publication Data

US 2013/0056516 A1 Mar. 7, 2013

Related U.S. Application Data

(63) Continuation of application No. 12/793,326, filed on Jun. 3, 2010, now Pat. No. 8,328,062.

(60) Provisional application No. 61/227,134, filed on Jul. 21, 2009.

(51) Int. Cl.
*A61B 17/10* (2006.01)
*A61B 17/04* (2006.01)
*A61B 17/115* (2006.01)
*A61B 17/072* (2006.01)

(52) U.S. Cl.
CPC ........... *A61B 17/115* (2013.01); *A61B 17/1155* (2013.01); *A61B 2017/07214* (2013.01)
USPC ..................................... 227/179.1; 227/181.1

(58) Field of Classification Search
USPC ............. 227/175.1–182.1; 606/139, 142, 143
See application file for complete search history.

(56) References Cited

U.S. PATENT DOCUMENTS

| | | | |
|---|---|---|---|
| 4,550,870 A | | 11/1985 | Krumme et al. |
| 5,188,636 A | * | 2/1993 | Fedotov .................... 606/144 |
| 5,441,193 A | * | 8/1995 | Gravener .................. 227/176.1 |
| 5,445,644 A | | 8/1995 | Pietrafitta et al. |
| 5,535,935 A | * | 7/1996 | Vidal et al. ................ 227/175.2 |
| 5,810,811 A | | 9/1998 | Yates et al. |
| 5,993,468 A | | 11/1999 | Rygaard |
| 6,024,748 A | | 2/2000 | Manzo et al. |
| 6,248,117 B1 | | 6/2001 | Blatter |

(Continued)

FOREIGN PATENT DOCUMENTS

| | | | |
|---|---|---|---|
| EP | 1 875 868 | 1/2008 | |
| EP | 1 875 870 | 1/2008 | |
| EP | 1875868 A1 | * 1/2008 | |
| EP | 1875870 A1 | * 1/2008 | ........... A61B 17/115 |

OTHER PUBLICATIONS

European Search Report for Application No. 10 25 12 94 dated Nov. 17, 2010 (7 pages).

*Primary Examiner* — Robert Long

(57) ABSTRACT

A surgical stapling instrument including a handle assembly, an elongated body portion, a shell assembly and an anvil assembly. The elongated body portion extends distally from the handle assembly and defines a longitudinal axis. The shell assembly is disposed adjacent a distal end of the elongated body portion and includes a non-planar, tissue-contacting surface oriented obliquely with respect to the longitudinal axis. The anvil assembly includes a non-planar, tissue-contacting surface oriented obliquely with respect to the longitudinal axis. The tissue-contacting surface of the anvil assembly is configured to align with the tissue-contacting surface of the shell assembly when the anvil assembly and shell assembly are in the approximated position.

13 Claims, 8 Drawing Sheets

(56) References Cited

U.S. PATENT DOCUMENTS

| | | | |
|---|---|---|---|
| 6,623,494 B1 | 9/2003 | Blatter | |
| 7,070,083 B2 | 7/2006 | Jankowski | |
| 7,220,237 B2 | 5/2007 | Gannoe et al. | |
| 7,220,268 B2 | 5/2007 | Blatter | |
| 7,229,428 B2 | 6/2007 | Gannoe et al. | |
| 7,422,138 B2 * | 9/2008 | Bilotti et al. | 227/179.1 |
| 7,608,073 B2 * | 10/2009 | Heinrich et al. | 606/50 |
| 7,651,017 B2 * | 1/2010 | Ortiz et al. | 227/176.1 |
| 7,988,028 B2 * | 8/2011 | Farascioni et al. | 227/180.1 |
| 7,997,468 B2 * | 8/2011 | Farascioni | 227/176.1 |
| 8,292,153 B2 * | 10/2012 | Jankowski | 227/176.1 |
| 8,393,513 B2 * | 3/2013 | Jankowski | 227/176.1 |
| 8,413,870 B2 * | 4/2013 | Pastorelli et al. | 227/179.1 |
| 2003/0014064 A1 | 1/2003 | Blatter | |
| 2004/0097994 A1 | 5/2004 | Blatter | |
| 2004/0176786 A1 | 9/2004 | Edoga et al. | |
| 2005/0187576 A1 | 8/2005 | Whitman et al. | |
| 2005/0189397 A1 * | 9/2005 | Jankowski | 227/176.1 |
| 2005/0209685 A1 | 9/2005 | Shifrin et al. | |
| 2005/0283191 A1 | 12/2005 | Fontayne et al. | |
| 2006/0167485 A1 | 7/2006 | Blatter | |
| 2006/0201989 A1 | 9/2006 | Ojeda | |
| 2006/0201992 A1 | 9/2006 | Racenet et al. | |
| 2006/0201993 A1 | 9/2006 | Hur | |
| 2007/0034668 A1 * | 2/2007 | Holsten et al. | 227/179.1 |
| 2007/0114261 A1 * | 5/2007 | Ortiz et al. | 227/175.1 |
| 2007/0175963 A1 | 8/2007 | Bilotti et al. | |
| 2010/0200641 A1 * | 8/2010 | Holsten et al. | 227/180.1 |
| 2012/0325893 A1 * | 12/2012 | Pastorelli et al. | 227/177.1 |

* cited by examiner

SURGICAL INSTRUMENT WITH CURVILINEAR TISSUE-CONTACTING SURFACES

CROSS REFERENCE TO RELATED APPLICATIONS

The present application is a Continuation Application of U.S. application Ser. No. 12/793,326, filed Jun. 3, 2010, which claims priority to U.S. Provisional Application Ser. No. 61/227,134, filed Jul. 21, 2009, the entire contents of which are incorporated herein by reference.

This application claims priority to provisional application Ser. No. 61/227,134, filed Jul. 21, 2009, the entire contents of which are incorporated herein by reference.

BACKGROUND

1. Technical Field

The present disclosure relates generally to a surgical stapling instrument for applying surgical staples to body tissue.

2. Background of Related Art

Anastomosis is the surgical joining of separate hollow tissue sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the tissue sections are joined by means of a stapling instrument which drives a circular array of staples through the end section of each tissue section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow tissue section(s) to be stapled are clamped between the anvil head and the staple holding component when these components are approximated. The clamped tissue is stapled by driving one or more staples from the staple holding component so that the ends of the staples pass through the tissue and are deformed by pockets or depressions in the anvil head. An annular knife is concurrently advanced to core tissue within the hollow tissue sections to free a tubular passage within the organ.

Besides anastomosis of hollow organs and tissue, surgical stapling instruments for performing circular anastomosis have been used to treat internal hemorrhoids in the rectum. Typically, during use of a circular stapling instrument for hemorrhoid treatment, the anvil head and the staple holding component of the surgical stapling instrument are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling instrument is fired to remove the hemorrhoidal tissue or tissue adjacent the hemorrhoidal tissue and staple the cut tissue.

SUMMARY

The present disclosure relates in one aspect to a surgical stapling instrument including a handle assembly, an elongated body portion, a shell assembly and an anvil assembly. The elongated body portion extends distally from the handle assembly and defines a longitudinal axis. The shell assembly is disposed adjacent a distal end of the elongated body portion and includes a non-planar, tissue-contacting surface oriented obliquely with respect to the longitudinal axis. The anvil assembly includes a non-planar, tissue-contacting surface oriented obliquely with respect to the longitudinal axis and aligned with the tissue contacting surface of the shell assembly in the approximated position.

In one embodiment, the tissue-contacting surface of the shell assembly and the tissue-contacting surface of the anvil assembly are each curvilinear along at least a portion of their lengths. In one embodiment, the curvilinear segments are separated by a concave point and a convex point. In one embodiment, the tissue-contacting surface of the anvil assembly and shell assembly includes at least one convexly curved section and at least one concavely curved section The shell assembly and the anvil assembly preferably create a staple line disposed obliquely with respect to the longitudinal axis. The shell assembly and the anvil assembly can create a substantially elliptical staple line.

In one embodiment, the anvil assembly includes an anvil rod detachably mountable to the surgical instrument.

In one embodiment, the tissue-contacting surface of the anvil assembly includes two curvilinear segments, each curvilinear segment being a substantially mirror image of the other.

DESCRIPTION OF THE DRAWINGS

Various embodiments of the presently disclosed surgical stapling instrument are disclosed herein with reference to the drawings, wherein.

DETAILED DESCRIPTION OF EMBODIMENTS

Figure 1:
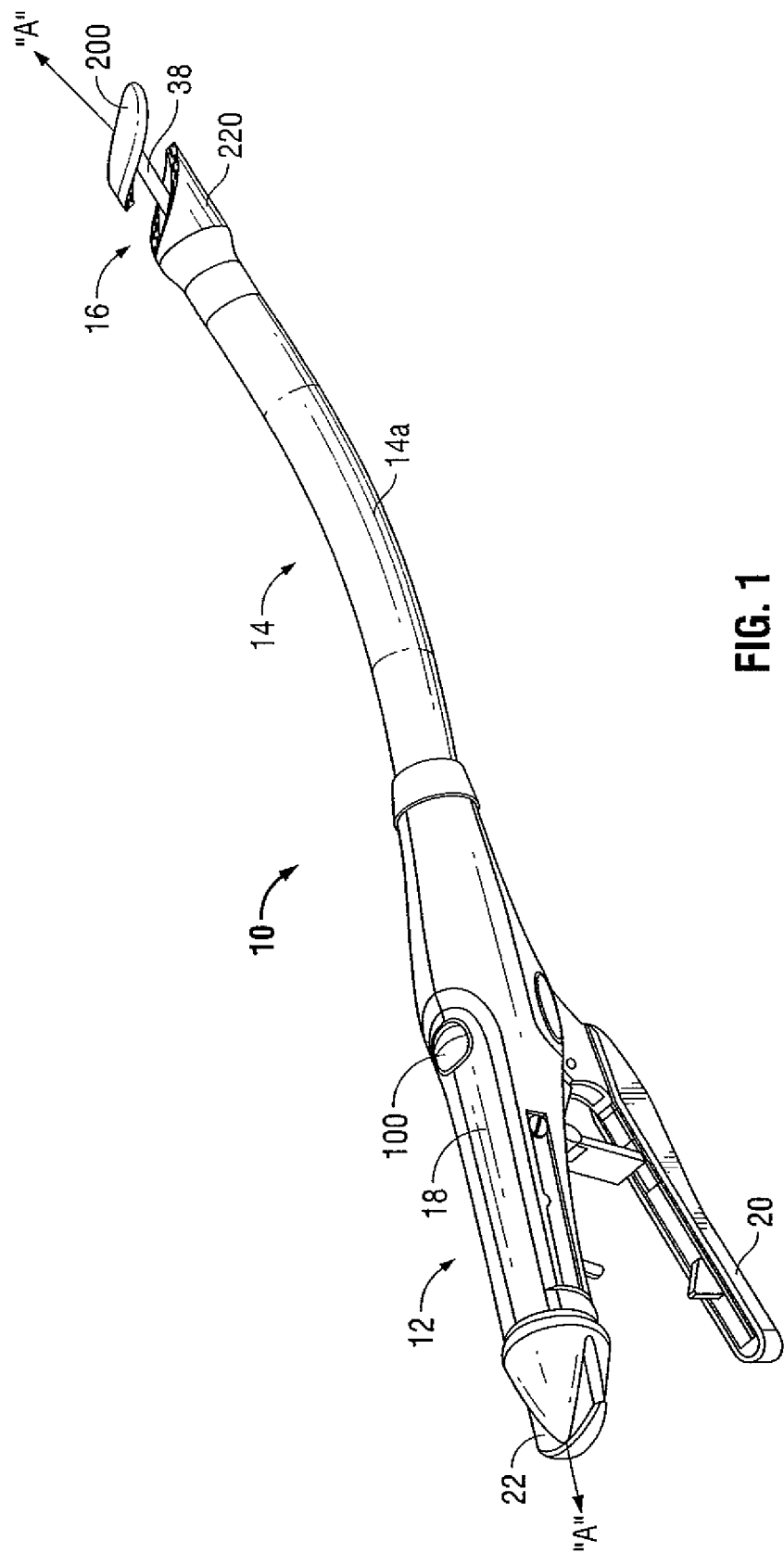
FIG. 1 is a perspective view of the presently disclosed surgical stapling instrument illustrated in an unapproximated position, in accordance with an embodiment of the present disclosure.

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument farther from the operator.

Figure 2:
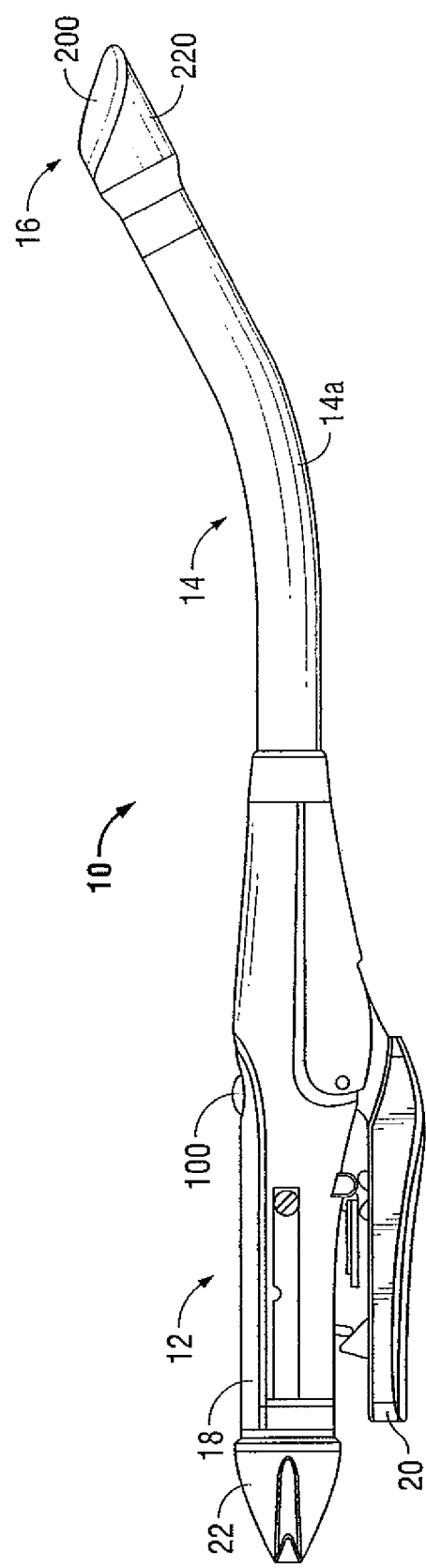
FIG. 2 is a side view of the surgical stapling instrument of FIG. 1 illustrated in an approximated position.

FIGS. 1-2 illustrate one embodiment of the presently disclosed surgical stapling instrument shown generally as 10. Briefly, surgical stapling instrument 10 includes a handle assembly 12, an elongated body portion 14 including a curved elongated outer tube 14a, and a head portion 16. Alternately, in some surgical procedures, e.g., the treatment of hemorrhoids, it is desirable to have a substantially straight body portion. The length, shape and/or the diameter of body portion 14 and head portion 16 may also be varied to suit patient size and/or a particular surgical procedure.

With continued reference to FIGS. 1-2, handle assembly 12 includes a stationary handle 18, a firing trigger 20, a rotatable approximation knob 22 and an indicator mechanism 100. Head portion 16 includes an anvil assembly 200 and a shell assembly 220. Anvil assembly 200 is movable in relation to shell assembly 220 between spaced and approximated positions.

With continued reference to FIGS. 1-2, in operation, rotation of approximation knob 22 causes movement of anvil assembly 200 in relation to shell assembly 220 between spaced (unapproximated) (FIG. 1) and approximated (FIG. 2) positions, as approximation knob 22 is mechanically engaged with an anvil retainer 38 (FIG. 1), which is fastened to anvil assembly 200. An anvil shaft of anvil assembly 200 is preferably removably mounted within anvil retainer 38 to removably connect the anvil assembly 200 to the stapling instrument. It is envisioned that rotation of approximation knob 22 in a first direction (e.g., clockwise) causes proximal movement of anvil assembly 200, and rotation of approximation knob 22 in a second opposite direction (e.g., counter-clockwise) causes distal movement of anvil assembly 200.

Figure 3:
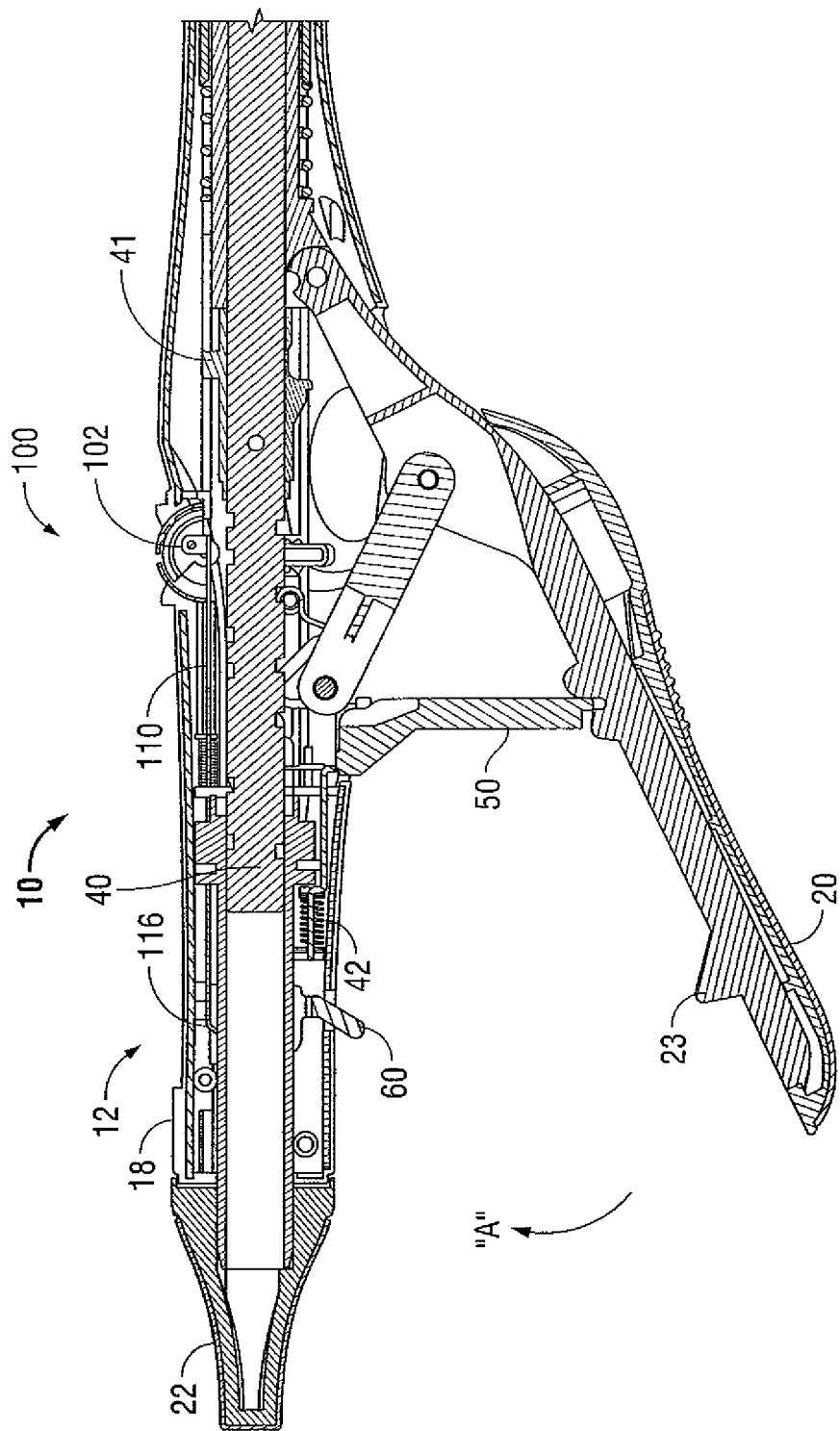
FIG. 3 is a longitudinal, cross-sectional view of a handle portion of the surgical stapling instrument of FIG. 1 in the unapproximated position.
Figure 4:
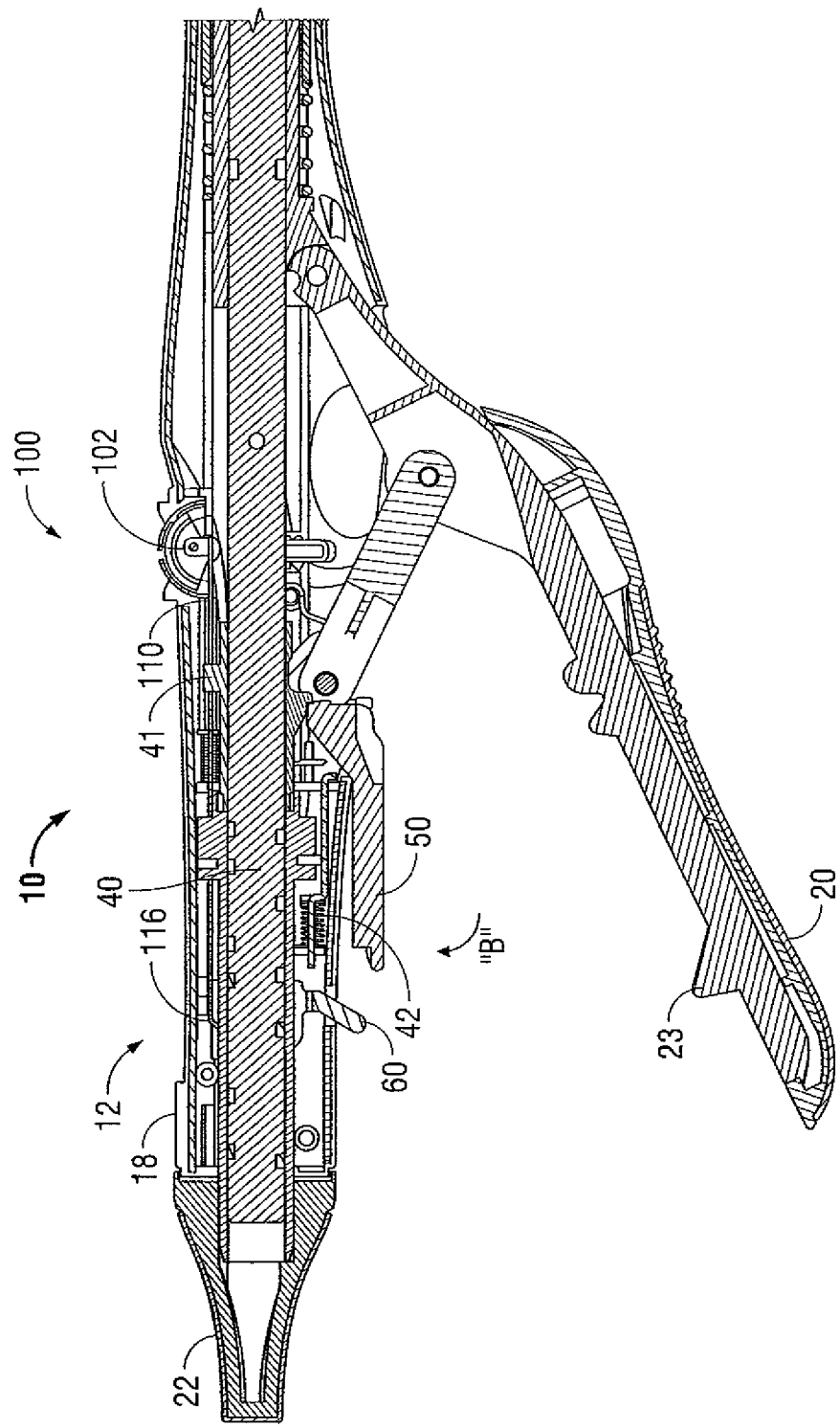
FIG. 4 is a longitudinal, cross-sectional view of the handle portion of the surgical stapling instrument of FIG. 1 in the approximated unfired position, of FIG. 2.
Figure 5:
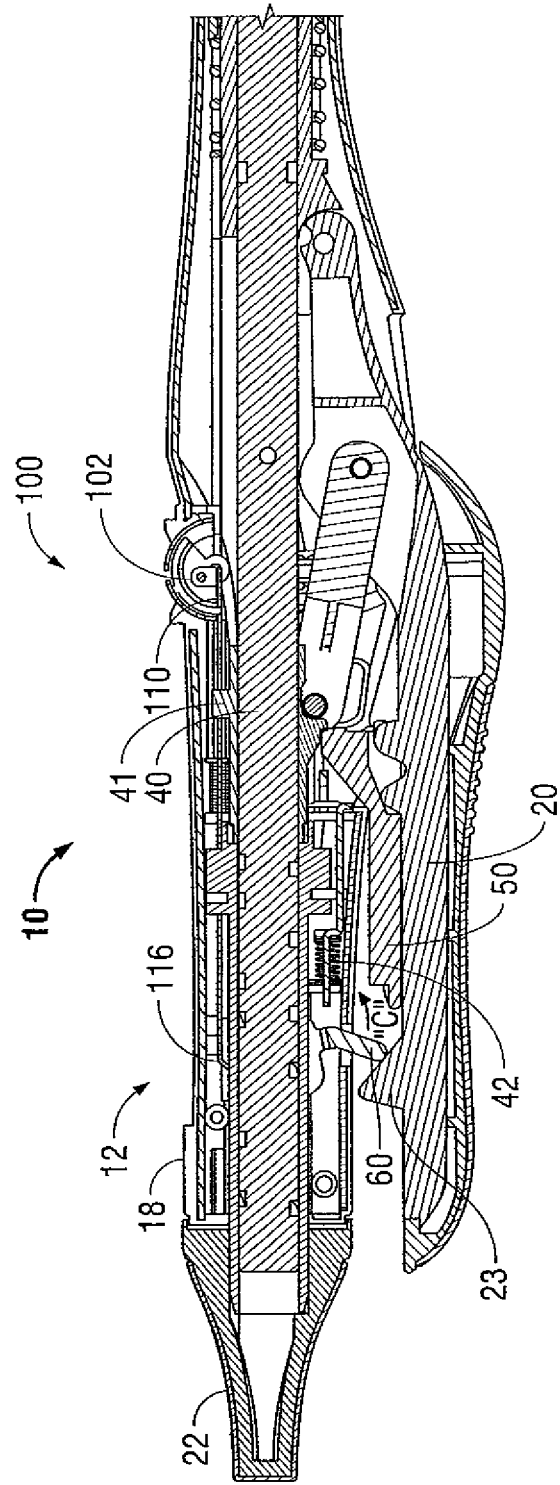
FIG. 5 is a longitudinal, cross-sectional view of the handle portion of the surgical stapling instrument of FIG. 1 in the fired position.
Figure 6:
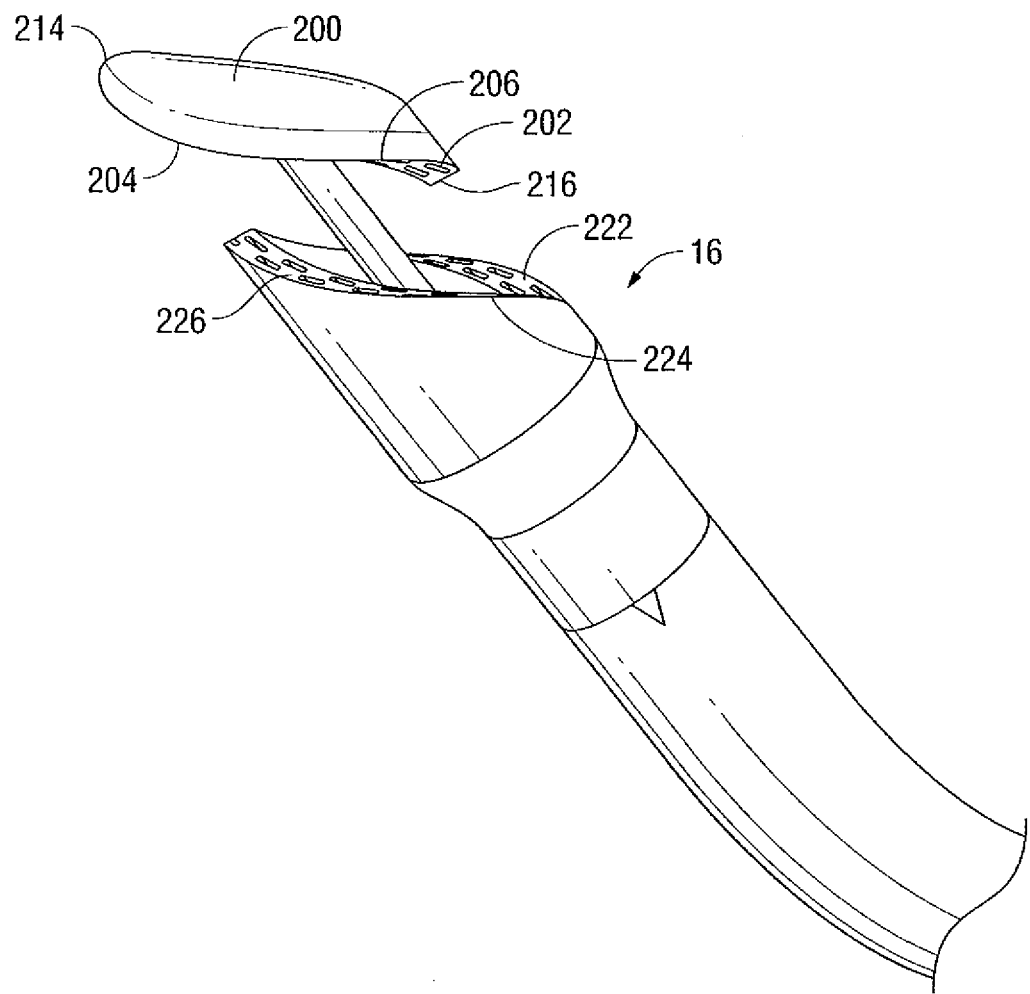
FIGS. 6 and 7 are perspective and side views, respectively, of the distal end of the surgical stapling instrument of FIG. 1 illustrated in the unapproximated position.
Figure 7:
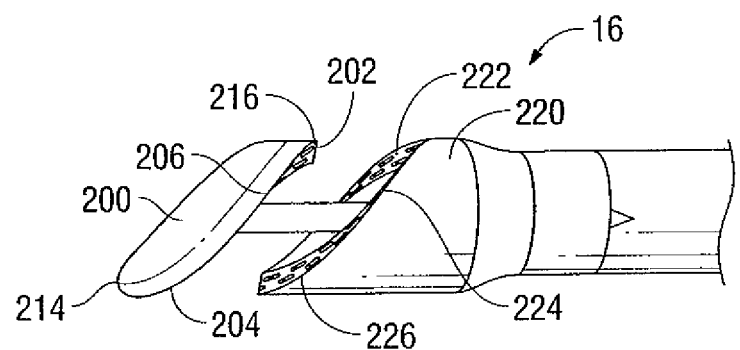

Referring now to FIGS. 3-5, approximation knob 22 is mechanically engaged with a spiral cam or screw stop 40, and screw stop 40 is in mechanical cooperation with anvil assembly 200. Rotation of approximation knob 22 in the first direction causes screw stop 40 to move proximally, which in turn causes proximal movement of anvil assembly 200, such approximation described in detail in U.S. Pat. No. 7,303,106, the entire contents of which are incorporated herein by reference.

Additionally, the embodiments illustrated in FIGS. 3-5 show a lockout mechanism including a trigger lock 50. Trigger lock 50 is disposed in mechanical cooperation with handle assembly 12 and maintains firing trigger 20 in an open position until anvil assembly 200 and shell assembly 220 have been approximated. As can be appreciated, the lockout mechanism helps prevent staples from being fired prematurely. More particularly, it is envisioned that as screw stop 40 moves proximally, a portion of screw stop 40 urges a portion of the lockout mechanism proximally against the bias of spring 42, thus allowing the pivoting of trigger lock 50 in the substantial direction of arrow "B" in FIG. 4 to permit firing of surgical stapling instrument 10.

With regard to indicator mechanism 100, it is envisioned that an indicator 102 is movable between a first position, which provides indication that the instrument 10 has not been approximated and is not in a fire-ready condition, a second position, which provides indication that the instrument has been approximated and is now in a fire-ready position, and third position, which provides indication that the instrument has been fired.

It is envisioned that during approximation of anvil assembly 200 with respect to shell assembly 220, a tab 41 of screw stop 40 passes through a slot of a slide member 110 and engages a proximal end of the slot. Continued approximation causes indicator 102 to pivot to its second position. The lockout mechanism and indicator mechanisms are disclosed in U.S. Pat. No. 7,303,106, the entire contents of which have previously been incorporated herein by reference.

A complete actuation of firing trigger 20 causes indicator 102 to pivot from its second position to its third position. Specifically, once firing trigger 20 is completely actuated, a tab 23 disposed on firing trigger 20 contacts a pawl 60 of stationary handle 18. The engagement between tab 23 and pawl 60 causes pawl 60 to rotate in the general direction of arrow "C" in FIG. 5. As pawl 60 rotates, a rib of pawl 60 contacts an extension 116 of slide member 110, causing proximal translation of slide member 110. As slide member 110 translates proximally, its mechanical engagement with indicator 102 causes indicator 102 to move to a third position. In the third position, indicator 102 provides indication to a surgeon that the instrument has been fired.

Actuation of firing trigger 20 (i.e., pivoting in the direction of arrow "A" in FIG. 3), causes staples to be ejected from shell assembly 220 distally towards anvil assembly 200. That is, firing trigger 20 is disposed in mechanical cooperation with a pusher (not explicitly shown in the illustrated embodiments), such that actuation of firing trigger 20 causes advancement of the pusher into contact with the staples to eject the staples into staple deforming pockets of anvil assembly 200. Such actuation is disclosed in U.S. Pat. No. 7,303,106, incorporated by reference above.

Figure 8:
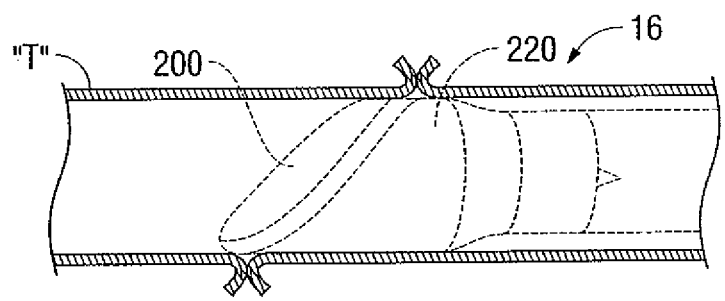
FIG. 8 is a perspective view of the distal end of the surgical stapling instrument of FIG. 1 illustrated in the approximated position clamping tissue.

Referring now to FIGS. 6-8 and 10-11, the head portion 16 of surgical stapling instrument 10 is shown in various stages of operation. More particularly, FIGS. 6, 7, 10 and 11 illustrate anvil assembly 200 and shell assembly 220 in the spaced, or unapproximated position and FIG. 8 illustrates anvil assembly 200 and shell assembly 220 in the approximated position. As illustrated, shell assembly 220 includes a non-planar (e.g., curvilinear), tissue-contacting surface 222 that is oriented obliquely with respect to a longitudinal axis "A-A" (FIG. 1) defined by elongated body portion 14. Additionally, anvil assembly 200 includes a non-planar (e.g., curvilinear), tissue-contacting surface 202 oriented obliquely with respect to the longitudinal axis "A-A." As shown (in FIG. 8, for example), the configuration of tissue-contacting surface 202 of anvil assembly 200 aligns with the configuration of the tissue-contacting surface 222 of shell assembly 220. That is, in the absence of tissue between the tissue contacting surfaces 202, 222, when anvil assembly 200 in its approximated position, it would matingly engage shell assembly 222. In use though, tissue is clamped between these two assemblies 200, 220.

With reference to FIGS. 6, 7, 10 and 11, tissue-contacting surface 202 of anvil assembly 200 comprises a complex curve with concave and convex surfaces. More specifically, surface 202 has an elongated shape such that the straight line distance from points 207a, 207b is greater than the straight line distance from points 209a, 209b. The surface 202 includes a curve having a convex portion 204, with convex end 207b, a concave portion 203a, 203b emanating from convex portion 204 on each side, then transitioning into another convex portion 208a, 208b extending to concave portion 205 with concave end 207a.

Tissue contacting surface 222 of shell assembly 220 comprises a complex curve with concave and convex surfaces. It has as elongated shape such that the straight line distance from points 227a, 227b is greater than the straight line distance from points 229a, 229b. The surface includes a curve having a concave portion 224 with a concave end 227b, a convex portion 226a, 226b emanating from the concave portion 224, then transitioning into another concave portion 228a, 228b extending to convex portion 225 with convex end 227a. The opening in the shell assembly is designated by reference numeral 229.

Figure 11:
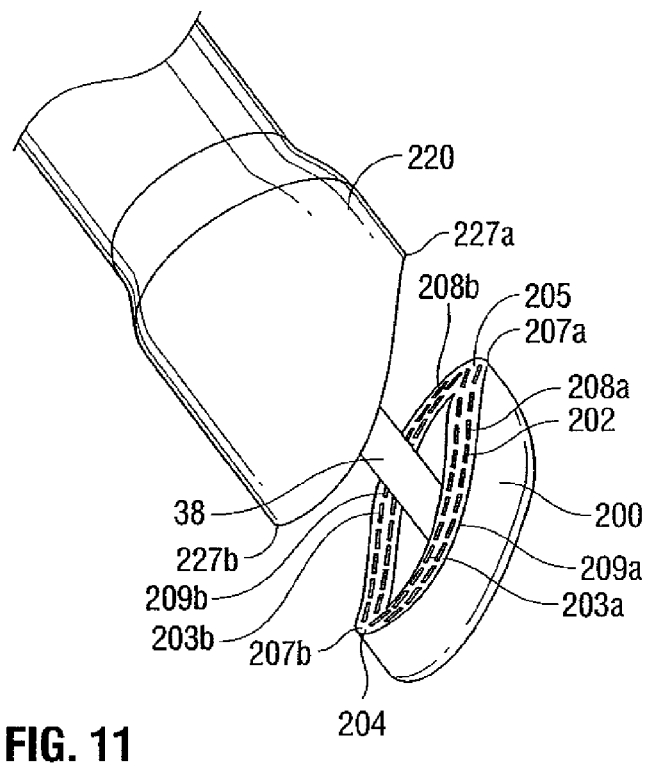

Thus, with particular reference to FIG. 11, viewed another way, tissue-contacting surface 202 of anvil assembly 200 includes two curvilinear segments which are separated by a concave end 207a and convex end 207b. Similarly, and with reference to FIG. 10, shell assembly 220 (e.g., tissue-contacting surface 222 thereof) includes two curvilinear segments, which are separated by a concave end 227b and a convex end 227a. As can be appreciated with reference to the Figures, concavity and convexity are with respect to the respective tissue-contacting surfaces of anvil assembly 200 and shell assembly 220. As can be appreciated, these multiple curves provide a helical "sweep" configuration or an S-like curve. Convex portion 204 of anvil assembly 200 is configured to align with concave portion 224 of shell assembly 220, and concave portion 205 of anvil assembly 200 is configured to align with convex portion 225 of shell assembly 220 when approximated. Such configuration provides the tissue-contacting surfaces with a ribbon-like shape. Consequently, the anvil assembly has first and second arrays of pockets to receive fasteners fired from the shell assembly, the first array lying in multiple non-parallel planes and the second array lying in multiple non-parallel planes. The shell assembly has a first and second array of fasteners wherein each array lies in multiple non-parallel planes.

Figure 9:
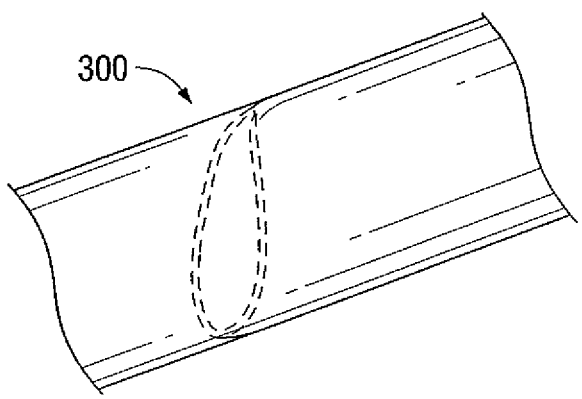
FIG. 9 is a plan view of a staple line resulting from the firing of the surgical stapling instrument of FIG. 1.
Figure 10:
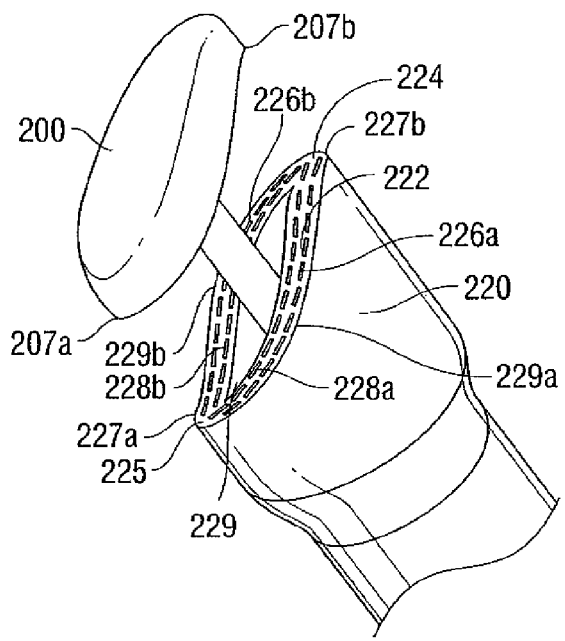
FIGS. 10 and 11 are perspective views of the distal end of the surgical instrument of FIG. 1 in the unapproximated position.

Referring now to FIG. 9, a staple line 300 is shown. The staple line that results from mating cooperation between anvil assembly 200 and shell assembly 220 is substantially elliptical (as shown) and is disposed obliquely (i.e., not perpendicular) with respect to longitudinal axis "A-A." As can be appreciated, staple line 300 having a substantially elliptical shape includes a greater cross-sectional area than a circular cross-section resulting from when the tissue-contacting surfaces of a shell and anvil are disposed perpendicularly with respect to a longitudinal axis. That is, the cross-sectional configuration of the staple line, i.e. substantially elliptical, created by utilization of the disclosed instrument 10 (and more specifically, head portion 16) increases the length of the staple line and due to its shape, when stricture occurs, it has a minimal affect on the reduction of the overall diameter of the staple line, thereby facilitating a patient's ability to pass waste.

Further details of other features of surgical instrument 10, such as the approximation assembly, firing assembly, lock out mechanism and indicator mechanism are disclosed in commonly-owned U.S. Pat. Nos. 7,168,604 and 7,303,106, the entire contents of each of which are incorporated by reference herein.

It will be understood that various modifications may be made to the embodiments disclosed herein. Therefore, the above description should not be construed as limiting, but merely as exemplifications of disclosed embodiments.

What is claimed is:

1. A surgical instrument, comprising:
a handle assembly;
an elongated body portion extending distally from the handle assembly and defining a longitudinal axis;
a first jaw member disposed adjacent a distal end of the elongated body portion, the first jaw member including a non-planar tissue-contacting surface; and
a second jaw member having a non-planar tissue-contacting surface, and the entirety of, the non-planar tissue-contacting surface of the second jaw member divided into exactly two curvilinear segments, each curvilinear segment including exactly one concave portion and exactly one convex portion,
wherein the tissue-contacting surface of the second jaw member is configured to align with the tissue-contacting surface of the first jaw member when the second jaw member and the first jaw member are in an approximated position.

2. The surgical instrument of claim 1, wherein the non-planar tissue-contacting surface of the first jaw member is divided into exactly two curvilinear segments, and wherein the curvilinear segments of the tissue-contacting surface of the first jaw member are separated by a concave point and a convex point.

3. The surgical instrument of claim 2, wherein the curvilinear segments of the tissue-contacting surface of the second jaw member are separated by a concave point and a convex point.

4. The surgical instrument of claim 1, wherein elongated body portion includes a longitudinally curved portion.

5. The surgical instrument of claim 1, wherein the tissue-contacting surface of the first jaw member is curvilinear along at least a majority of its length.

6. The surgical instrument of claim 5, wherein the tissue-contacting surface of the second jaw member is curvilinear along at least a majority of its length.

7. The surgical instrument of claim 1, wherein the second jaw member includes first and second arrays of pockets to receive fasteners fired from the first jaw member, the first array lying in multiple non-parallel planes.

8. The surgical instrument of claim 1, wherein the first jaw member includes first and second arrays of fasteners at least partially therein, each array lying in multiple non-parallel planes.

9. The surgical instrument of claim 1, wherein the second jaw member includes a rod detachably mountable to the surgical instrument.

10. The surgical instrument of claim 1, wherein the two curvilinear segments of the tissue-contacting surface of the second jaw member are substantially mirror images of each other.

11. The surgical instrument of claim 10, wherein the non-planar tissue-contacting surface of the first jaw member is divided into exactly two curvilinear segments, and wherein the two curvilinear segments of the tissue-contacting surface of the first jaw member are substantially mirror images of each other.

12. The surgical instrument of claim 1, wherein the tissue-contacting surface of the first jaw member is oriented obliquely with respect to the longitudinal axis.

13. The surgical instrument of claim 12, wherein the tissue-contacting surface of the second jaw member is oriented obliquely with respect to the longitudinal axis.

* * * * *